(12) United States Patent
Son et al.

(10) Patent No.: US 10,507,170 B2
(45) Date of Patent: Dec. 17, 2019

(54) OPEN POROUS ORGANIC-INORGANIC COMPOSITE POWDER, METHOD FOR PREPARING SAME, AND COSMETIC COMPOSITION CONTAINING SAME

(71) Applicants: COSMAX, INC., Gyeonggi-do (KR); Korea Advanced Institute of Science and Technology, Daejeon (KR)

(72) Inventors: Ho Yeon Son, Daejeon (KR); Yoon Sung Nam, Daejeon (KR); Ji Hui Jang, Gyeonggi-do (KR); Su Ji Kim, Gyeonggi-do (KR); Jun Bae Lee, Gyeonggi-do (KR); Myeong-Sam Park, Seoul (KR)

(73) Assignees: COSMAX, INC., Gyeonggi-do (KR); Korea Advanced Institute of Science and Technology, Daejeon (KR)

( * ) Notice: Subject to any disclaimer, the term of this patent is extended or adjusted under 35 U.S.C. 154(b) by 80 days.

(21) Appl. No.: 15/772,494

(22) PCT Filed: Sep. 21, 2016

(86) PCT No.: PCT/KR2016/010532
§ 371 (c)(1),
(2) Date: Apr. 30, 2018

(87) PCT Pub. No.: WO2017/078266
PCT Pub. Date: May 11, 2017

(65) Prior Publication Data
US 2019/0076337 A1 Mar. 14, 2019

(30) Foreign Application Priority Data
Nov. 3, 2015 (KR) .................. 10-2015-0153697

(51) Int. Cl.
| | | |
|---|---|---|
| *A61K 8/02* | (2006.01) | |
| *A61K 8/27* | (2006.01) | |
| *A61K 8/29* | (2006.01) | |
| *A61Q 19/00* | (2006.01) | |
| *A61K 8/60* | (2006.01) | |
| *A61K 8/37* | (2006.01) | |
| *A61K 8/19* | (2006.01) | |
| *A61K 8/34* | (2006.01) | |
| *A61K 8/81* | (2006.01) | |
| *A61Q 17/04* | (2006.01) | |

(52) U.S. Cl.
CPC ............ *A61K 8/022* (2013.01); *A61K 8/0241* (2013.01); *A61K 8/19* (2013.01); *A61K 8/27* (2013.01); *A61K 8/29* (2013.01); *A61K 8/347* (2013.01); *A61K 8/37* (2013.01); *A61K 8/602* (2013.01); *A61K 8/8152* (2013.01); *A61Q 19/00* (2013.01); *A61K 2800/10* (2013.01); *A61K 2800/413* (2013.01); *A61K 2800/612* (2013.01); *A61Q 17/04* (2013.01)

(58) Field of Classification Search
CPC .. A61K 2800/413; A61K 8/0241; A61K 8/29; A61K 8/347; A61K 8/8152
See application file for complete search history.

(56) References Cited

FOREIGN PATENT DOCUMENTS

| | | |
|---|---|---|
| KR | 10-0378521 B1 | 3/2003 |
| KR | 10-2008-0091653 A | 10/2008 |
| KR | 10-0986262 B1 | 10/2010 |
| KR | 10-1261784 B1 | 5/2013 |
| KR | 10-2014-0030395 A | 3/2014 |
| KR | 10-1470850 B1 | 12/2014 |

OTHER PUBLICATIONS

Du et al., "Complete UV Emission of ZnO Nanoparticles in a PMMA Matrix.",*Semiconductor Science and Technology*, Jul. 12, 2006, vol. 21. pp. I202-1206.
Ejima, et al., "One-Step Assembly of Coordination Complexes for Versatile Film and Particle Engineering." *Science*. 341 (6142), 154-157. (Jul. 12, 2013) DOI: 10.1126/science.1237265.
Fan et al., "Surface-initiated Polymerization from TiO2 Nanoparticle Surfaces through a Biomimetic Initiator: A New Route toward Polymer-matrix Nanocomposites.", *Composites Science and Technology*, (Electronic publishing) Nov. 15, 2005, vol. 66, No. 9, pp. 1195-1201.
Kim, et al. "Titanium dioxide/poly(methyl methacrylate) composite microspheres prepared by in situ suspension polymerization and their ability to protect against UV rays." *Colloid Polym. Sci.* (2002) 280: 584-588. DOI 10.1007/s00396-002-0655-6.
Rahim, et al. "Coordination-Driven Multistep Assembly of Metal-Polyphenol Filmsand Capsules." *Chem. Mater.*, 26:1645-1653. (2014) dx.doi.org/10.1021/cm403903m.
Yuwono et al.. "Transparent Nanohybrids of Nanocrystalline TiO2 in PMMA with Unique Nonlinear Optical Behavior.", *Journal of Materials Chemistry*, (Electronic publishing) Apr. 16, 2003, vol. 13, pp. 1475-1479.
International Search Report dated Jan. 5, 2017, issued in International Patent Application No. PCTKR2016010532, with English Translation.
International Written Opinion dated Jan. 5, 2017, issued in International Patent Application No. PCTKR2016010532, with English Translation.

*Primary Examiner* — Nannette Holloman
(74) *Attorney, Agent, or Firm* — Harness, Dickey & Pierce, P.L.C.

(57) ABSTRACT

The present invention provides a method for preparing porous organic/inorganic composite powder which includes attaching inorganic oxide nanoparticles in a multi-layer form by repeating steps of attaching polyphenol to porous polymethyl methacrylate (PMMA) microspheres and attaching inorganic oxide nanoparticles to the porous polymethyl methacrylate (PMMA) microspheres to which polyphenol is attached, and a cosmetic composition including the porous organic/inorganic composite powder.

10 Claims, 7 Drawing Sheets

OPEN POROUS ORGANIC-INORGANIC COMPOSITE POWDER, METHOD FOR PREPARING SAME, AND COSMETIC COMPOSITION CONTAINING SAME

CROSS-REFERENCE TO RELATED APPLICATIONS

This application is a national phase application of PCT Application No. PCT/KR2016/010532, filed on Sep. 21, 2016, which claims the benefit and priority of Korean Application No. 10-2015-0153697 2015, filed on Nov. 3, 2015. The entire disclosures of the applications identified in this paragraph are incorporated herein by reference.

FIELD

The present invention is made with a subject number of NRF-2014M1A8A1049303 under the support of Korean Ministry of Science, ICT and Future Planning, and the supervisory management organ of the subject is National Research Foundation of Korea, the subject business title is "Macroscience Research and Development Business", the subject title is "Development of Carbon dioxide-Converted Nanowire-Based Hybrid Photocatalyst", the supervisor organ is Korea Institute of Science and Technology, and the research period is Jun. 1, 2014-May 31, 2017.

In addition, the present invention is made with a subject number of S2341055 under the support of Korean Ministry of SMEs and Startups, and the supervisory management organ of the subject is Korea Institute for Advancement of Technology (KIAT), the subject business title is "World Class 300 R&D", the subject title is "Development of skin-cell receptor ligands and novel transdermal delivery system for K-Cosmetic functional products", the supervisor organ is COSMAX, and the research period is Sep. 1, 2013-Aug. 31, 2017.

The present invention relates to a method for preparing porous organic/inorganic composite powder and a cosmetic composition including the same. More particularly, the present invention relates to a method for preparing porous organic/inorganic composite powder which includes attaching inorganic oxide nanoparticles in a multi-layer form by repeating steps of attaching polyphenol to porous polymethyl methacrylate (PMMA) microspheres and attaching inorganic oxide nanoparticles to the porous polymethyl methacrylate (PMMA) microspheres to which polyphenol is attached, and a cosmetic composition including the porous organic/inorganic composite powder.

Particularly, the present invention relates to a method for preparing porous organic/inorganic composite powder which includes attaching inorganic oxide nanoparticles in a multi-layer form by attaching polyphenol to porous polymethyl methacrylate (PMMA) microspheres, attaching inorganic oxide nanoparticles to the porous polymethyl methacrylate (PMMA) microspheres to which polyphenol is attached, and repeating steps of attaching polyphenol and attaching inorganic oxide nanoparticles to the resultant product including polyphenol and inorganic oxide nanoparticles attached thereto.

BACKGROUND

Polymethyl methacrylate (PMMA) is one of the polymerizates of methyl methacrylate. In the cosmetic field, PMMA has been used widely for production of fundamental cosmetics and makeup cosmetics by virtue of its matte feeling of use and high oil absorption. Particularly, since powder including PMMA has excellent sebum adsorption ability, it has been used widely for fundamental cosmetics for controlling sebum and makeup cosmetic products for amending a skin tone. In addition, an effect of amending a skin tone can be expected by virtue of a soft focusing effect derived from scattered reflection of light. It is known that such powder has a porous structure in order to realize the above-mentioned effects.

Many patents have been published to date about technologies of supporting a sunscreen by using porous or hollow particles. According to such technologies, an organic sunscreen is supported by dipping porous or hollow particles in the organic sunscreen.

Particularly, Korean Patent Publication No. 1261784 discloses a method for forming a composite pigment phase by mixing porous spherical PMMA with ethylhexyl methoxycinnamate with a high-speed mixer (title: 'Organic Sunscreen-Supported Functional PMMA Composite Pigment, Method for Preparing The Same and Sunscreen Cosmetic Composition Including The Same). However, when an organic sunscreen is supported with and enclosed in a porous polymer, the organic sunscreen may be absorbed into the skin to cause skin irritation and a product formed through photoreaction may cause skin irritation. In addition, an organic sunscreen has low photostability, and thus there is a disadvantage in that it should be applied repeatedly with the lapse of time. In addition, Korean Patent Publication No. 0378521 (title: The method for preparation of sun protecting complex powder') relates to a technology of coating and incorporating titanium oxide to the inner/outer part of powder by activating the inner/outer part of powder with an acid, and hydrolyzing titanium alkoxide at the inner/outer part of powder in situ. However, in this case, a strong acid, such as nitric acid or hydrochloric acid, is used to form OH groups in the inner/outer part of powder and $TiO_2$ is synthesized directly by using a sol-gel process through heating at high temperature. Thus, such a condition using a strong acid and high temperature may cause a safety-related problem undesirably when using the composite powder is used as a cosmetic material.

Moreover, although an inorganic material, such as titanium oxide ($TiO_2$) or zinc oxide (ZnO), used as a conventional inorganic sunscreen material has an excellent sunscreen effect, it has high polarity and large specific gravity and has a problem of agglomeration and precipitation in a formulation, and thus shows a limitation in that it causes a white turbidity and undergoes degradation of its unique excellent sunscreen effect. To solve the above-mentioned problems, a study has been conducted to enclose an inorganic material, such as titanium oxide or zinc oxide, in PMMA microspheres (Colloid Polym Sci, 2002, 280, 584-588). However, since such a structure does not have a porous structure contributing to reduction of specific gravity significantly, there is a limitation in that reduction of specific gravity cannot be accomplished while a number of inorganic material particles are agglomerated in the microspheres.

Under these circumstances, the inventors of the present invention have attempted a method which includes preparing porous PMMA microspheres first and then coating $TiO_2$ nanoparticles to the surface of the voids by using polyphenol, in order to solve the above-mentioned problems. In general, it is known that polyphenol is contained in foods, such as wine, chocolate, tea leaves and persimmon, and is able of absorbing UV light. It is also reported that polyphenol can form a strong bonding with a metal ion (Science 2013 341:154). Although a patent (KR10-2010-0025762)

and article (Chem. Mater., 2014, 26, 1645-1653) about coating technologies using polyphenol and a nanometal based on the above-mentioned characteristics were published, they are not directed to coating the voids of a porous structure capable of scattering light with an inorganic material as disclosed herein, and they are not intended to be applied to cosmetics requiring low specific gravity and high dispersion stability on the basis of an improved sunscreen effect of an organic/inorganic composite material of polyphenol and titanium dioxide.

The inventors of the present invention have developed a method for coating the voids and surface of a porous polymer support having excellent dispersibility with $TiO_2$ nanoparticles and polyphenol in a multi-layer form, in order to overcome the problems of the related art. When using the method, it is possible to incorporate materials that can be bound with polyphenol simultaneously into a porous support, besides $TiO_2$ nanoparticles. In addition, the inventors of the present invention have developed a novel sunscreen material having excellent dispersibility and an improved sunscreen effect by using the porous polymer microspheres coated with $TiO_2$ nanoparticles and polyphenol. Since the composite is coated uniformly with the inorganic sunscreen in the material, there is little agglomeration of the inorganic sunscreen so that the sunscreen effect may be improved, and there is an advantage in that the material is safer in terms of skin irritation as compared to a polymer including an organic sunscreen. In addition, there is an advantage in that the content of $TiO_2$ nanoparticles and that of polyphenol can be controlled with ease depending on number of coating times.

After the inventors of the present invention have conducted many studies to overcome the above-mentioned problems according to the related art, we have found that when porous organic/inorganic composite powder is prepared by repeating steps of attaching polyphenol to porous polymethyl methacrylate (PMMA) microspheres and attaching inorganic oxide nanoparticles to the porous polymethyl methacrylate (PMMA) microspheres to which polyphenol is attached so that inorganic oxide nanoparticles may be attached in a multi-layer form, it is possible to obtain porous organic/inorganic composite powder including an inorganic material attached uniformly on the surface of a porous organic polymer support. We have also found that when the porous organic/inorganic composite powder prepared from the above-mentioned method is applied to sunscreen cosmetics, it is possible to attach the inorganic particles used as a sunscreen uniformly to the support and to prevent agglomeration of the particles, and thus the inorganic sunscreen is allowed to maintain their unique excellent characteristics and provides an excellent sunscreen effect. The present invention is based on these findings.

SUMMARY OF INVENTION

Technical Problem

A technical problem to be solved by the present invention is to provide a method for preparing porous organic/inorganic composite powder which includes attaching an inorganic material uniformly to the surface of an organic polymer support to obtain porous organic/inorganic composite powder.

Another technical problem to be solved by the present invention is to provide a cosmetic composition including the porous organic/inorganic composite powder obtained by using the method for preparing porous organic/inorganic composite powder.

Technical Solution

In one general aspect, there is provided a method for preparing porous organic/inorganic composite powder, which includes the steps of:

(a) attaching polyphenol to porous polymethyl methacrylate (PMMA) microspheres;

(b) attaching inorganic oxide nanoparticles to the resultant product of step (a); and (c) subjecting the resultant product of step (b) to attachment of polyphenol and attachment of inorganic oxide nanoparticles repeatedly so that inorganic oxide nanoparticles may be attached in a multi-layer form.

Technologies of supporting a sunscreen using porous or hollow particles are known according to the related art. However, there is a problem in that the sunscreen is an organic sunscreen to cause skin irritation. In addition, an inorganic sunscreen causes little skin irritation, has an excellent sunscreen effect and is used widely as a sunscreen material. However, such an inorganic sunscreen has a problem of agglomeration and precipitation in a formulation, and thus is problematic in that it causes white turbidity and undergoes degradation of its unique excellent sunscreen effect. Moreover, although some studies have been conducted about incorporation of an inorganic material into porous particles, the above-mentioned problems still cannot be solved.

Under these circumstances, in order to solve the above-mentioned problems, the inventors of the present invention have developed a method for preparing porous organic/inorganic composite powder which includes coating polymethyl methacrylate (PMMA) microspheres with polyphenol and an inorganic material in a multi-layer form, and a cosmetic composition including the same and having an excellent sunscreen effect.

According to an embodiment of the present invention, tannic acid is used as polyphenol in step (a). Tannic acid has five branches containing a galloyl group having three hydroxyl groups on a benzene ring. When using tannic acid, it is possible to form a colorless and very thin adhesive layer on the surfaces of various materials, such as organic or inorganic materials. Coating with tannic acid is allowed on various surfaces, including hydrophilic or hydrophobic surfaces, and can be used as a method for introducing a functional nanomaterial to various surfaces at room temperature under ambient pressure by virtue of strong adhesion capability and sufficient reduction ability capable of reducing metal ions. In step (a) of attaching tannic acid to porous PMMA microspheres, a number of hydroxyl groups contained in tannic acid are bound with carbonyl groups of PMMA through hydrogen bonding or the like. In this manner, tannic acid is adsorbed to the surface of porous PMMA microspheres.

According to another embodiment of the present invention, in step (a), polyphenol may be attached to the porous polymethyl methacrylate microspheres by mixing them at a weight ratio of porous polymethyl methacrylate microspheres:polyphenol of 20:1-5:2, preferably at a weight ratio of polymethyl methacrylate microspheres:polyphenol of 15:1-5:1. When the concentration of polyphenol is too low, it is not possible to carry out coating over the whole surface of the microspheres. When the concentration of polyphenol is too high, waste of polyphenol not coated on the microspheres is increased undesirably.

According to still another embodiment of the present invention, polyphenol in step (a) may be catechin, epigalocatechin, epigalocatechin galate, epicatechin galate, tannic acid, catechol, resveratrol or quercetin, preferably tannic acid, catechol, resveratrol or quercetin. According to an embodiment of the present invention, tannic is used but the scope of the present invention is not limited thereto.

According to still another embodiment of the present invention, inorganic oxide in step (b) may be cerium oxide ($CeO_2$), iron oxides ($Fe_2O_3$, $Fe_3O_4$), zirconium oxide ($ZrO_2$), silica ($SiO_2$), titanium dioxide ($TiO_2$), iridium dioxide ($IrO_2$) or zinc oxide (ZnO), preferably titanium dioxide ($TiO_2$), iridium dioxide ($IrO_2$) or zinc oxide (ZnO). According to an embodiment of the present invention, titanium dioxide ($TiO_2$) is used but the scope of the present invention is not limited thereto.

In addition, inorganic oxide attached after the coating with tannic acid may be various inorganic nanoparticles in addition to $TiO_2$. In other words, inorganic oxide may include at least one inorganic oxide selected from the group consisting of cerium oxide ($CeO_2$), iron oxides ($Fe_2O_3$, $Fe_3O_4$), zirconium oxide ($ZrO_2$), silica ($SiO_2$), titanium dioxide ($TiO_2$), iridium dioxide ($IrO_2$) and zinc oxide (ZnO). It is possible to obtain functional organic/inorganic hybrid structures through attachment of various inorganic nanoparticles using the coating with tannic acid.

According to still another embodiment of the present invention, inorganic oxide in step (b) may be nanoparticles synthesized through a sol-gel process. Particularly, titanium isopropoxide and tetrabutylammonium hydroxide may be used as a titanium precursor and alkaline salt, respectively, for the purpose of synthesis of $TiO_2$ nanoparticles. This allows production of elongated $TiO_2$ nanoparticles having a width of about 3-10 nm and a length of about 50-200 nm. However, various methods for synthesizing $TiO_2$ nanoparticles may be used and the above-mentioned method does not limit the scope of the present invention.

According to still another embodiment of the present invention, inorganic oxide may be attached to the product of step (a) or (b) by mixing inorganic oxide with the product at a weight ratio of the product:inorganic oxide of 20:1-5:2, preferably at a weight ratio of the product:inorganic oxide of 15:1-5:1. When the concentration of inorganic oxide polyphenol is too low, it is not possible to carry out coating over the whole surface of the microspheres. When the concentration of inorganic oxide is too high, waste of inorganic oxide not coated on the microspheres is increased undesirably.

According to still another embodiment of the present invention, attachment of polyphenol and attachment of inorganic oxide to the product of step (b) are repeated once to four times, in step (c).

According to the test examples of the present invention, when adding porous PMMA microspheres coated with tannic acid to a dispersion of $TiO_2$ nanoparticles and mixing them at room temperature in step (b), $TiO_2$ nanoparticles can be adsorbed to the surface of the microspheres. Particularly, OH groups of tannic acid and Ti cations (i.e., $Ti^{4+}$) present on the surface of $TiO_2$ nanoparticles form strong bonds through the formation of ligand-to-metal charge transfer (LMCT) complex between them. In addition, it can be seen that the product shows a yellow color through such bonds (see, Test Example 1, FIG. 3 and FIG. 4). Further, it is possible to increase the amount of $TiO_2$ nanoparticles adsorbed to the surface of porous PMMA microspheres by repeating the coating with tannic acid and adsorption of $TiO_2$ nanoparticles in a layer-by-layer form through the strong binding force of the metal-ligand bonds between tannic acid and $TiO_2$ nanoparticles. In this manner, coating with tannic acid and $TiO_2$ can be carried out in a layer-by-layer form so that multilayered inorganic nanostructures may be attached to the surface of an organic support.

In another general aspect, there is provided a cosmetic composition including the porous organic/inorganic composite powder obtained by the above-described method.

It is shown that the porous organic/inorganic composite powder obtained by the method according to the present invention not only has an excellent sunscreen effect but also enhances the effect of another sunscreen. When the porous organic/inorganic composite powder is incorporated to a cosmetic composition, the cosmetic composition can be used as one having an excellent sunscreen effect.

According to the test examples of the present invention, after measuring in vitro sun protection factors (SPF) to determine sunscreen effects, the cosmetic composition (Test sample 4) containing the porous organic/inorganic composite powder according to the present invention shows an increased in vitro SPF value as compared to the formulations (Test sample 2) containing conventional $TiO_2$ powder and the control. This suggests that the cosmetic composition according to the present invention provides an improved sunscreen effect. As can be seen from the results, the porous organic/inorganic composite powder used as a sunscreen ingredient according to the present invention is suitable for a cosmetic composition capable of providing an improved sunscreen effect.

Herein, the cosmetic composition has at least one formulation selected from the group consisting of lotion, cream, powder, eye shadow, blusher, lipstick, makeup base, primer, foundation, BB cream, CC cream, sun cream and sun lotion.

The cosmetic composition obtained by using the product according to the present invention optionally includes other ingredients used conventionally in a cosmetic composition. Such ingredients include oil and fat ingredients, moisturizing agents, emollients, surfactants, organic and inorganic pigments, organic powder, UV absorbing agents, preservatives, sterilizing agents, anti-oxidants, plant extract, pH modifiers, alcohols, colorants, fragrances, blood flow stimulators, cooling agents, anti-hydrotics, purified water, or the like. In addition, the cosmetic composition according to the present invention may further include other active ingredients used conventionally in a cosmetic composition and particular examples of such ingredients include conventional adjuvants and carriers, such as stabilizers, solubilizers, vitamins, pigments and fragrances.

Advantageous Effects

As described above, it is possible to obtain porous organic/inorganic composite powder by attaching an inorganic material uniformly to the surface of a porous organic polymer support. When the porous organic/inorganic composite powder obtained as mentioned above is applied to a sunscreen product, the inorganic particles used as a sunscreen are attached uniformly to the support to prevent agglomeration of particles. Thus, it is possible to maintain the excellent characteristics unique to the inorganic sunscreen and to provide an excellent sunscreen effect.

DETAILED DESCRIPTION

Figure 1:
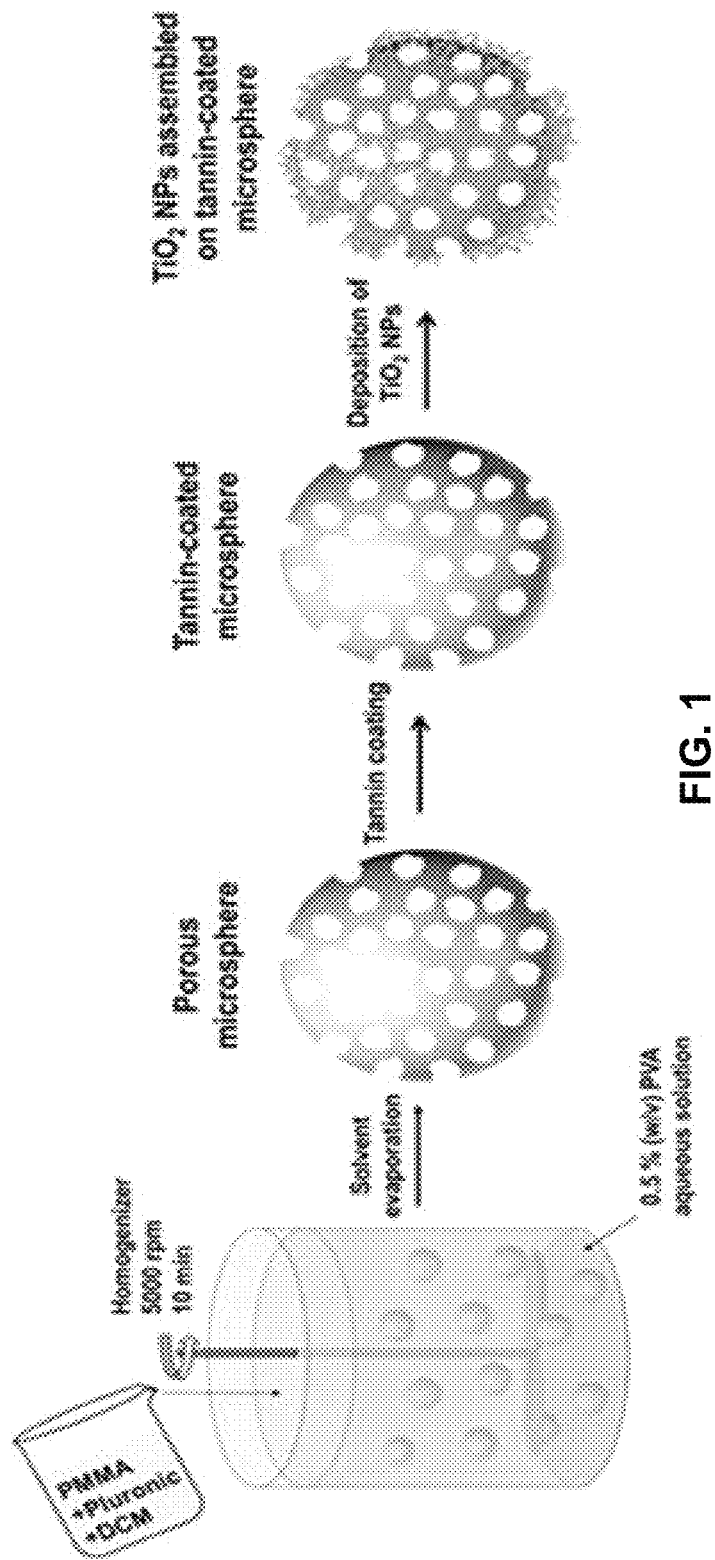
FIG. 1 is a flow chart illustrating a method for preparing a colloidal organic/inorganic sunscreen material obtained by using a porous organic/inorganic composite using polyphenol.
Figure 2:
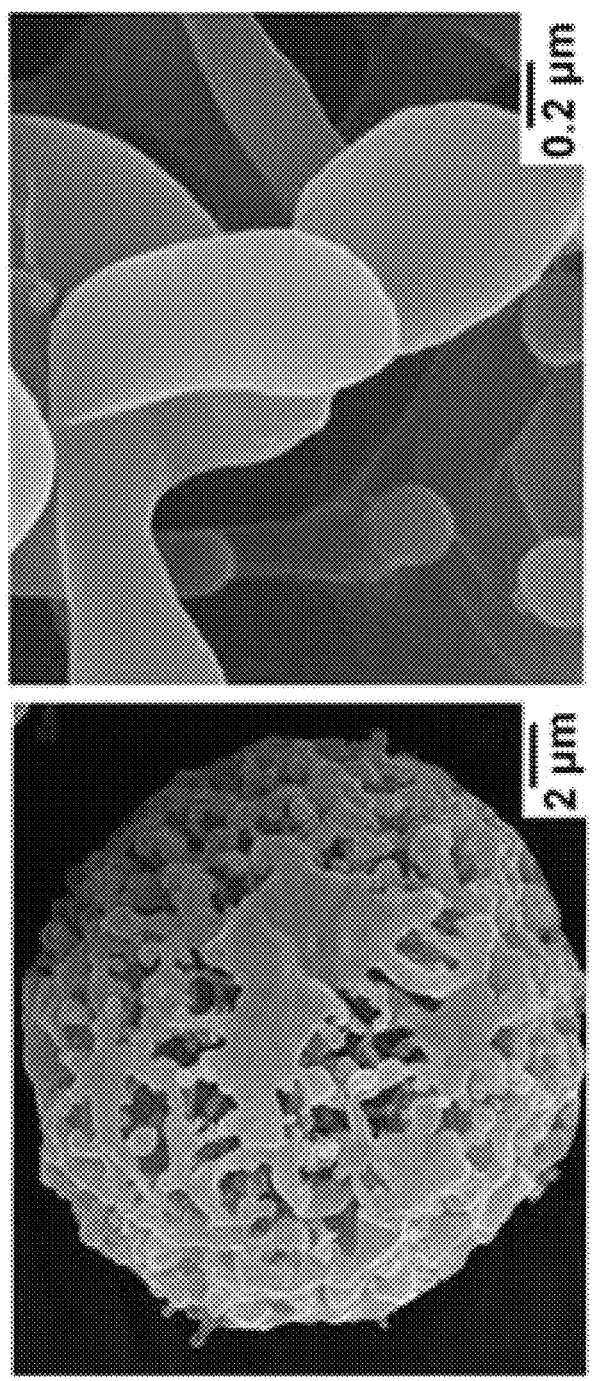
FIG. 2 is a scanning electron microscopic (SEM) image illustrating the appearance of porous polymethyl methacrylate (PMMA) microspheres, after they are coated with tannic acid.
Figure 3:
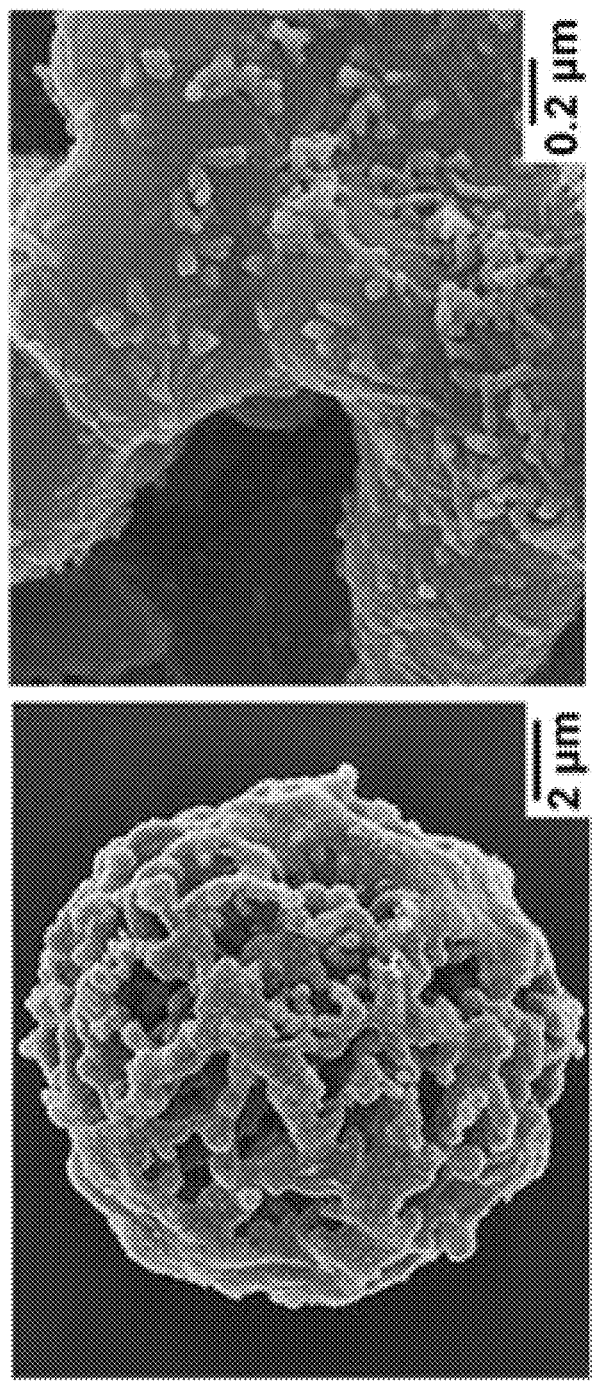
FIG. 3 is a SEM image illustrating porous PMMA microspheres coated with tannic acid, after they are coated with $TiO_2$.
Figure 4:
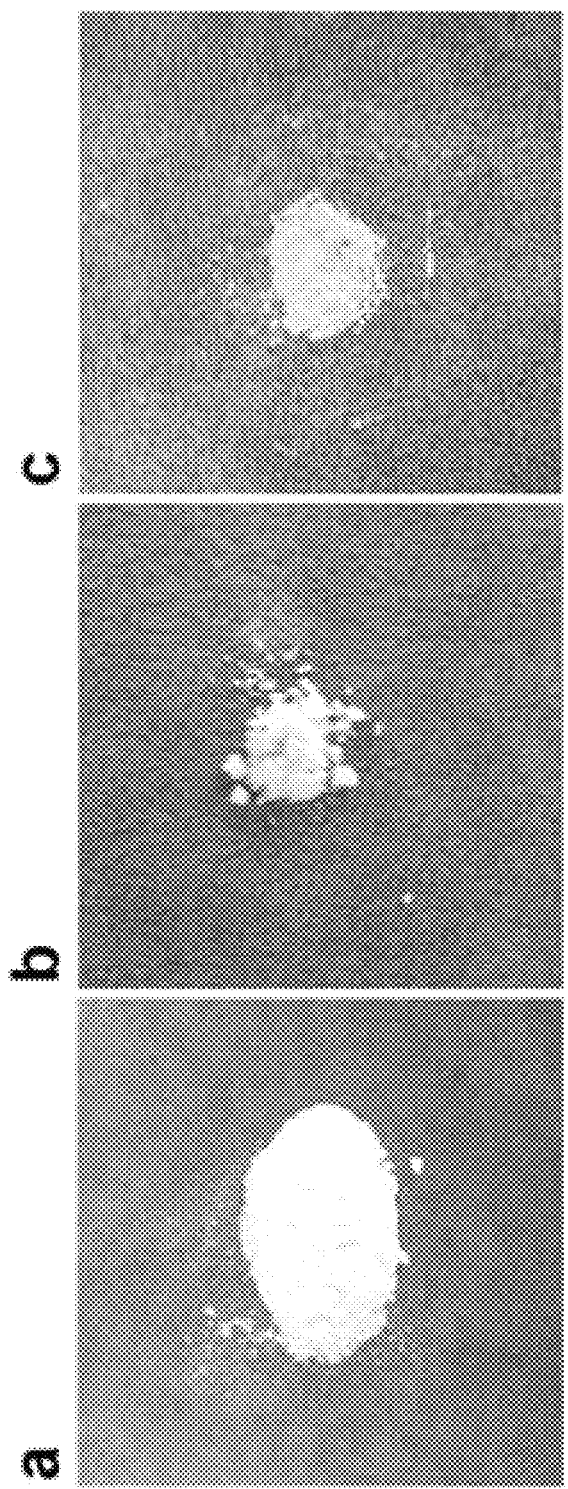
FIG. 4 shows the images illustrating variations in appearance of (a) porous PMMA microspheres, (b) the PMMA microspheres after they are coated with tannic acid, and (c) the PMMA microspheres after they are coated with $TiO_2$ nanoparticles.
Figure 5:
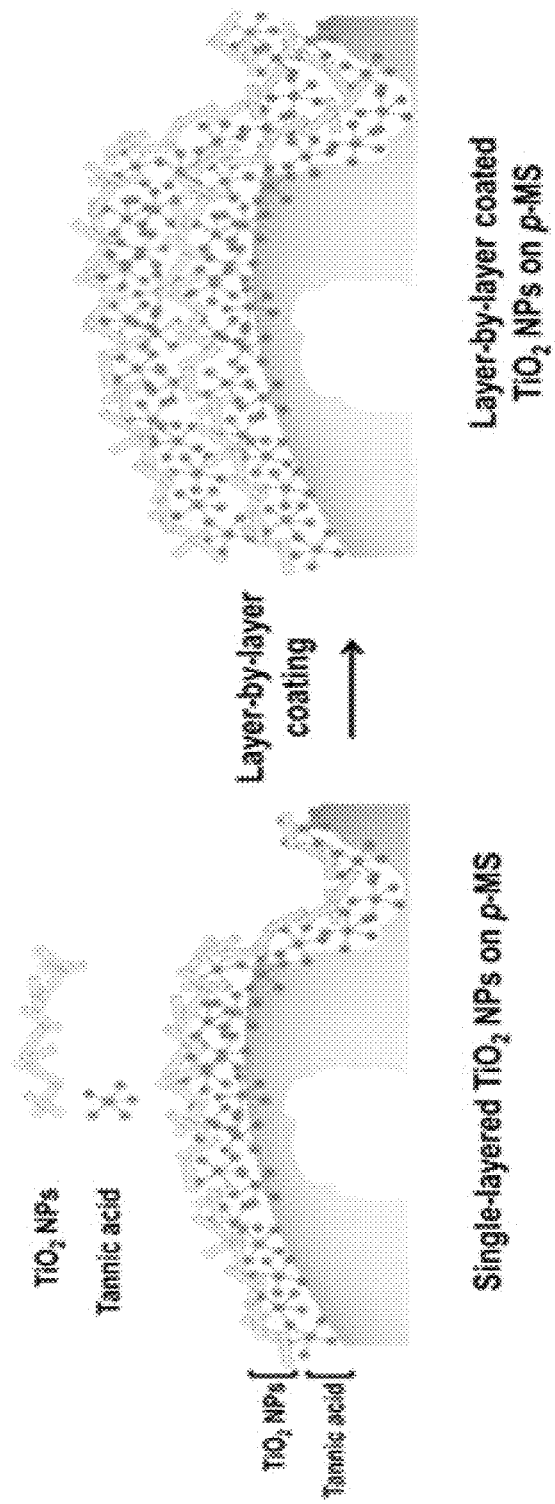
FIG. 5 is a schematic view illustrating a coating process with $TiO_2$ nanoparticles.
Figure 6:
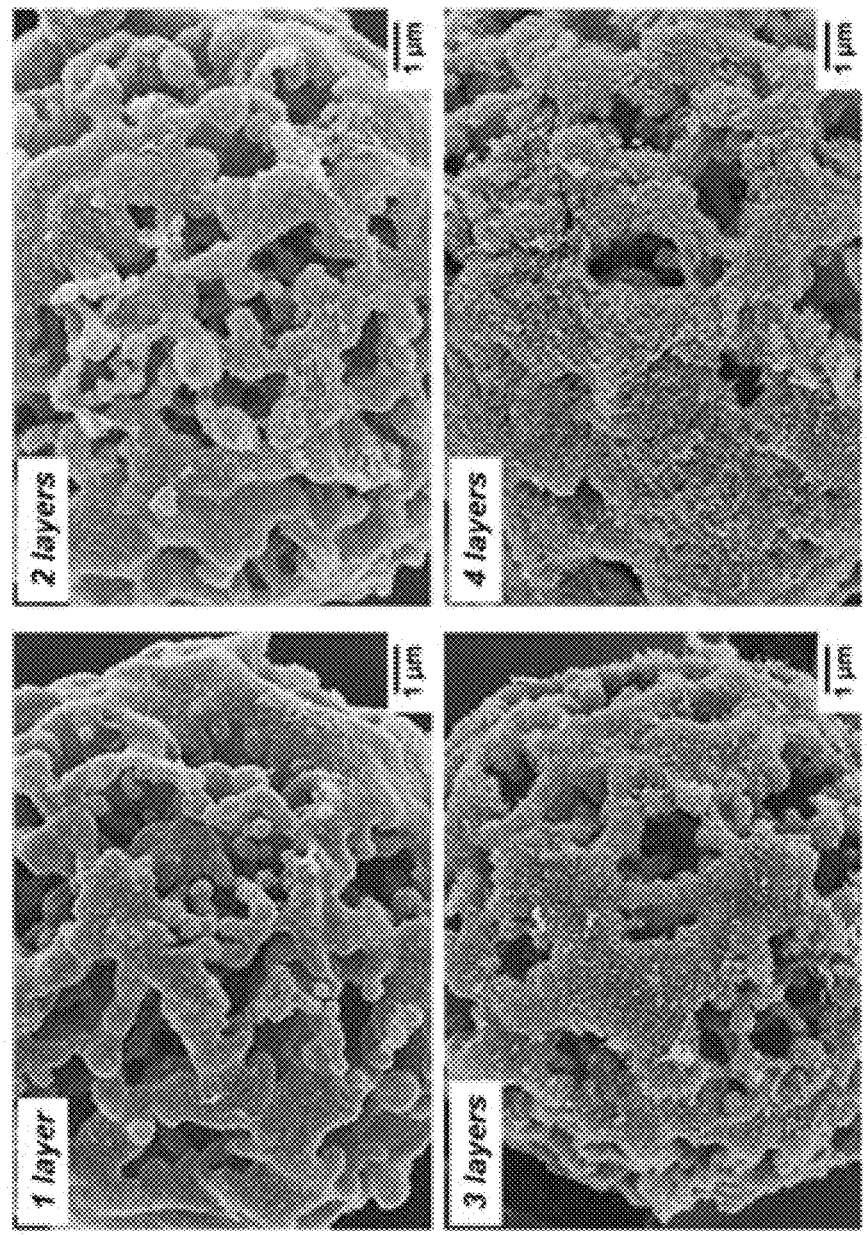
FIG. 6 is a SEM image illustrating porous PMMA microspheres while varying a number of coating times with $TiO_2$ nanoparticles.

Exemplary embodiments now will be described more fully hereinafter. The present invention may, however, be embodied in many different forms and should not be construed as limited to the exemplary embodiments set forth therein.

The present invention relates to a method for preparing a porous PMMA polymer to which inorganic oxide is adsorbed by coating porous PMMA microspheres with polyphenol and coating the resultant product with metal oxide in a layer-by-layer form. Herein, polyphenol is commercially available tannic acid (Sigma Aldrich No. 403040), the porous PMMA microspheres are those obtained by the applicant's published patent (Korea Patent Publication No. 10-1470850 titled 'Manufacturing method of macroporous Polymethyl methacrylate'), and detailed description thereof is omitted herein.

EXAMPLES

Example 1: Attachment of Tannic Acid to PMMA Porous Microspheres

First, 200 mg of PMMA (molecular weight: 50,000) porous microspheres were introduced to and dispersed in 38 mL of distilled water. Next, 20 mg of tannic acid was dissolved in 2 mL of distilled water. Then, the tannic acid solution was introduced to the preliminarily formed dispersion of PMMA porous microspheres and the reaction mixture was agitated rapidly for 5 minutes by using a vortex mixer. After 20 mL of ethanol was added to and mixed with the reaction mixture, centrifugal separation was carried out at 1,000 g for 5 minutes to cause precipitation. Then, the supernatant was removed and a mixed solution containing 20 mL of distilled water and 10 mL of ethanol was introduced to carry out redispersion. After that, the resultant dispersion was introduced to a 50 mL tube and centrifugal separation was carried out at 1,000 g for 5 minutes to cause precipitation. The above washing procedure was repeated twice in order to remove tannic acid remaining after the centrifugal separation.

Example 2: Attachment of $TiO_2$ Nanoparticles to PMMA Porous Microspheres Including Tannic Acid Attached Thereto The porous PMMA microspheres including tannic acid attached thereto as described in Example 1 were dispersed into 20 mL of distilled water. Next, 20 mg of $TiO_2$ nanoparticles were dispersed into distilled water. Then, the dispersion of $TiO_2$ nanoparticles was introduced to the dispersion of PMMA porous microspheres including tannic acid attached thereto and agitation was carried out for 3 hours by using a magnetic stirrer. After 20 mL of ethanol was introduced to and mixed with the reaction mixture, centrifugal separation was carried out at 1,000 g for 5 minutes to cause precipitation. After that, the supernatant was removed and a mixed solution containing 20 mL of distilled water and 10 mL of ethanol was introduced to carry out redispersion. After that, the resultant dispersion was introduced to a 50 mL tube and centrifugal separation was carried out at 1,000 g for 5 minutes to cause precipitation. The above washing procedure was repeated twice.

Example 3: Preparation of PMMA Porous Microspheres Having Multilayer Structure of $TiO_2$ Nanoparticles The porous PMMA microspheres including $TiO_2$ attached thereto as described in Example 2 were introduced to and dispersed in 38 mL of distilled water, and tannic acid solution prepared by dissolving 20 mg of tannic acid into 2 mL of distilled water was used to carry out attachment of tannic acid in the same manner as Example 1. Then, attachment of $TiO_2$ nanoparticles was carried out in the same manner as Example 2. Attachment of tannic acid and attachment of $TiO_2$ nanoparticles were repeated through layer-by-layer assembly to obtain PMMA porous microspheres having a multilayer structure of $TiO_2$ nanoparticles.

Test Example 1: Physical Property Values of $TiO_2$-Coated Porous PMMA Microspheres Depending on Number of $TiO_2$ Coating Times After preparing $TiO_2$-coated porous PMMA microspheres through the steps as described in Example 1-Example 3, the appearance, particle sizes and coating degrees were determined.

The determination was carried out as follows.

Tannic Acid Coating:

The amount of tannic acid adsorbed to porous PMMA microspheres was determined by using absorption spectra for tannic acid solutions before and after coating with tannic acid through UV-Vis absorption spectrometry.

$TiO_2$ Coating:

It was shown by the naked eyes that the microspheres showed a yellow color through metal-ligand binding between titanium and tannic acid after the adsorption of $TiO_2$ nanoparticles. Adsorption of $TiO_2$ nanoparticles, adsorption behavior thereof and the appearance of porous microspheres depending on number of $TiO_2$ coating times were determined through scanning electron microscopic images. The amount of $TiO_2$ adsorbed to the microspheres was analyzed by thermogravimetry analysis (TGA).

UV-Vis Absorption Spectrometry:

Differences in absorptivity depending on multiple coating of $TiO_2$ could be determined through UV-Vis absorption spectrometry. It was shown that absorptivity in the UV region was increased significantly as the amount of $TiO_2$ nanoparticles adsorbed in a layer-by-layer form was increased. The results of UV-Vis absorption spectrometry show that the $TiO_2$-adsorbed PMMA porous microspheres absorb light in a wavelength region of 400 nm or less (particularly at about 235 nm and about 295 nm). Comparison of absorptivity depending on coating times was carried out based on the above wavelengths.

The following Table 1 shows the physical properties of the porous PMMA microspheres before coating with $TiO_2$ and after 4 times of coating. BET analysis was carried out to analyze specific surface areas and weight ratios of $TiO_2$ nanoparticles for porous PMMA microspheres and the porous PMMA microspheres after carrying out coating with tannic acid and coating with $TiO_2$ nanoparticles 4 times.

TABLE 1

|  | No coating | 4 times of coating |
| --- | --- | --- |
| Specific surface area ($m^2 g^{-1}$) | 9.84 | 54.15 |
| Weight ratio of $TiO_2$ nanoparticles (%) | 1.2 | 30.4 |

After the test, the $TiO_2$-adsorbed nanoparticles showed a significant increase in specific surface area. It is though that this results from a mesoporous structure formed by $TiO_2$ nanoparticles on the surface of porous microspheres.

In addition, after TGA analysis was carried out to determine the weight ratio of $TiO_2$ nanoparticles for the porous PMMA microspheres subjected to 4 times of coating with tannic acid and adsorption of $TiO_2$ nanoparticles, it was shown that $TiO_2$ nanoparticles occupy about 30% of the total weight. This suggests that most of the $TiO_2$ nanoparticles introduced to the microspheres were adsorbed thereto.

The following Table 2 shows differences in UV absorptivity depending on $TiO_2$ coating times.

TABLE 2

|  | No coating | Coating once | Coating twice | Coating three times | Coating four times |
| --- | --- | --- | --- | --- | --- |
| Absorptivity at 235 nm | 0.195 | 0.284 | 0.303 | 0.417 | 1.253 |
| Absorptivity at 295 nm | 0.172 | 0.219 | 0.241 | 0.341 | 1.233 |

After the test, it can be seen that absorptivity tends to increase as the number of coating times increases from 1 to 4, since the amount of $TiO_2$ in the binding between tannic acid and $TiO_2$ is increased in proportion to the number of coating times, absorptivity is increased by $TiO_2$ and absorptivity is also increased by the binding between tannic acid and $TiO_2$.

Test Example 2: Demonstration of Effect of Boosting In Vitro SPF of $TiO_2$-Coated Porous PMMA An efficacy test about the effect of boosting in vitro SPF was carried out for the porous PMMA coated with $TiO_2$ nanoparticles four times as described in Example 3 by using an in vitro SPF analyzer. The following Table 3 shows the main ingredients, including a sunscreen, of sun cream formulation used for the test.

TABLE 3

| Main ingredients (%) | Control | Test sample 1 | Test sample 2 | Test sample 3 | Test sample 4 |
| --- | --- | --- | --- | --- | --- |
| Ethylhexyl Methoxycinnamate | 6.7 | 6.7 | 6.7 | 6.7 | 6.7 |
| Ethylhexyl Salicylate | 2.5 | 2.5 | 2.5 | 2.5 | 2.5 |

TABLE 3-continued

| Main ingredients (%) | Control | Test sample 1 | Test sample 2 | Test sample 3 | Test sample 4 |
| --- | --- | --- | --- | --- | --- |
| Diethylamino Hydroxybenzoyl Hexyl Benzoate | 1.5 | 1.5 | 1.5 | 1.5 | 1.5 |
| PMMA | — | 2 | — | — | — |
| $TiO_2$ | — | — | 0.6 | — | — |
| Porous PMMA | — | — | — | 2 | — |
| $TiO_2$ coated porous PMMA | — | — | — | — | 2 |

In vitro SPF (sun protection factor) analysis was carried out for the PMMA powder (Test sample 1) used for preparing microspheres in order to evaluate a sunscreen effect, $TiO_2$ powder (Test sample 2), porous PMMA microspheres (Test sample 3) and porous PMMA microspheres (Test sample 4) subjected to adsorption of $TiO_2$ nanoparticles 4 times. The test was carried out by applying the formulation uniformly to a PMMA plate (Helioplate HD6) and measuring SPF by using UV-2000S in vitro Sunscreen analyzer available from Labsphere Co. six times repeatedly. The results are shown in the following Table 4.

TABLE 4

|  | Control | Test sample 1 | Test sample 2 | Test sample 3 | Test sample 4 |
| --- | --- | --- | --- | --- | --- |
| in vitro SPF | 29.36 | 35.43 | 35.02 | 39.61 | 51.24 |
| Standard deviation | 5.30 | 3.43 | 1.78 | 3.66 | 12.21 |

Figure 7:
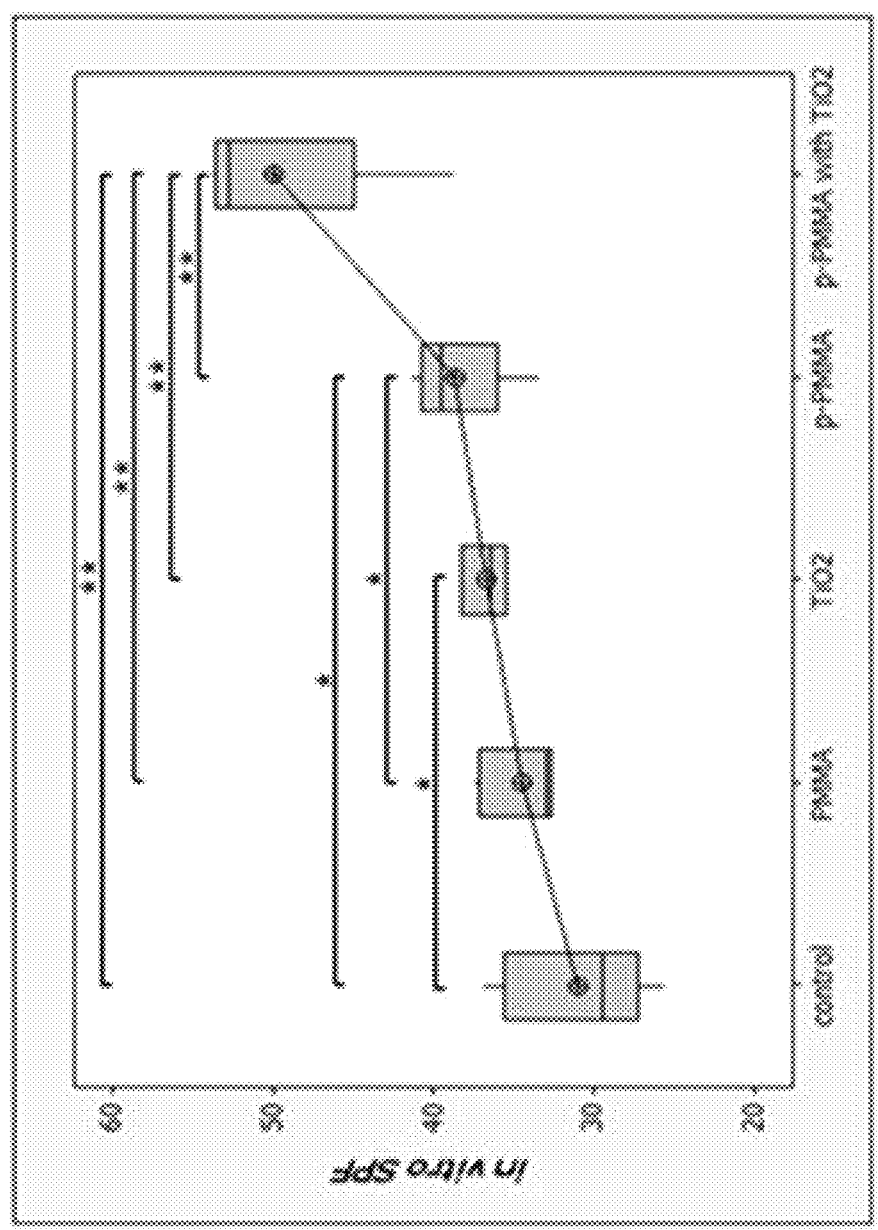
FIG. 7 is a graph illustrating a difference in in vitro SPF depending on $TiO_2$ coating.

The test results about in vitro SPF are shown in Table 4 and FIG. 7. The values obtained by repeating the test 6 times for the control and test samples were used to obtain averages and standard deviations. After the test, the raw material, PMMA powder itself, shows no SPF boosting effect and $TiO_2$ powder shows a SPF boosting effect as a UV protecting material. The porous PMMA microspheres show a SPF boosting effect as compared to the control. It is thought that UV light is weakened in the porous structure. The porous PMMA microspheres including $TiO_2$ nanoparticles adsorbed thereto shows the highest SPF boosting effect. It is thought that the highest effect results from not only weakening of UV light in the porous structure but also UV absorption caused by $TiO_2$ nanoparticles. Particularly, as compared to $TiO_2$ powder itself, the porous PMMA microspheres including $TiO_2$ nanoparticles adsorbed thereto cause no secondary agglomeration of $TiO_2$, and thus $TiO_2$ is dispersed uniformly without agglomeration. As a result, it is possible to obtain a higher SPF boosting effect.

INDUSTRIAL APPLICABILITY

As described above, the method according to the present invention allows a functional inorganic material to be attached uniformly to the surface of a colloidal organic polymer support having excellent dispersibility. Thus, the present invention can provide a base for developing a colloidal organic/inorganic composite material having excellent dispersibility, and can be applied widely to a functional material for cosmetics and coating materials.

What is claimed is:

1. A method for preparing porous organic/inorganic composite powder, which comprises the steps of:
   (a) attaching polyphenol to porous polymethyl methacrylate (PMMA) microspheres;
   (b) attaching inorganic oxide nanoparticles to the resultant product of step (a); and
   (c) subjecting the resultant product of step (b) to attachment of polyphenol and attachment of inorganic oxide nanoparticles repeatedly so that inorganic oxide nanoparticles may be attached in a multi-layer form.

2. The method for preparing porous organic/inorganic composite powder according to claim 1, wherein polyphenol is attached to the porous polymethyl methacrylate microspheres by mixing them at a weight ratio of polymethyl methacrylate microspheres:polyphenol of 20:1-5:2, in step (a).

3. The method for preparing porous organic/inorganic composite powder according to claim 1, wherein polyphenol in step (a) is tannic acid, catechol, resveratrol or quercetin.

4. The method for preparing porous organic/inorganic composite powder according to claim 1, wherein inorganic oxide in step (b) is titanium dioxide ($TiO_2$), iridium dioxide ($IrO_2$) or zinc oxide (ZnO).

5. The method for preparing porous organic/inorganic composite powder according to claim 1, wherein inorganic oxide in step (b) is one synthesized through a sol-gel process.

6. The method for preparing porous organic/inorganic composite powder according to claim 1, wherein inorganic oxide is attached to the product of step (a) or (b) by mixing inorganic oxide with the product at a weight ratio of the product:inorganic oxide of 20:1-5:2.

7. The method for preparing porous organic/inorganic composite powder according to claim 1, wherein steps (a) and (b) are repeated once to four times.

8. A cosmetic composition comprising the porous organic/inorganic composite powder obtained by the method as defined in claim 1.

9. The cosmetic composition according to claim 8, which has a sunscreen effect.

10. The cosmetic composition according to claim 8, which has at least one formulation selected from the group consisting of lotion, cream, powder, eye shadow, blusher, lipstick, makeup base, primer, foundation, sun cream and sun lotion.

* * * * *